US00PP22163P2

(12) United States Plant Patent
Dekker

(10) Patent No.: US PP22,163 P2
(45) Date of Patent: Sep. 27, 2011

(54) ***CHRYSANTHEMUM* PLANT NAMED 'DEKTOSHKA RED'**

(50) Latin Name: *Chrysanthemum×morifolium*
Varietal Denomination: Dektoshka Red

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/798,023

(22) Filed: Mar. 27, 2010

(51) Int. Cl.
*A01H 5/00* (2006.01)

(52) U.S. Cl. ..... Plt./298

(58) Field of Classification Search ..... Plt./298
See application file for complete search history.

*Primary Examiner* — June Hwu
(74) *Attorney, Agent, or Firm* — C. A. Whealy

(57) ABSTRACT

A new and distinct cultivar of *Chrysanthemum* plant named 'Dektoshka Red', characterized by its large daisy-type inflorescences with dark red-colored ray florets; strong, thick and upright flowering stems; uniform flowering habit; and good postproduction longevity.

2 Drawing Sheets

Botanical designation: *Chrysanthemum×morifolium.*
Cultivar denomination: 'DEKTOSHKA RED'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Dektoshka Red'.

The new *Chrysanthemum* plant is a naturally-occurring whole plant mutation of *Chrysanthemum×morifolium* 'Dektoshka', not patented. The new *Chrysanthemum* plant was discovered and selected by the Inventor as a single flowering plant within a population of plants of 'Dektoshka' in a controlled greenhouse environment in Hensbroek, The Netherlands in September, 2007.

Asexual reproduction of the new *Chrysanthemum* plant by terminal cuttings in a controlled greenhouse environment in Hensbroek, The Netherlands since October, 2007, has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dektoshka Red'. These characteristics in combination distinguish 'Dektoshka Red' as a new and distinct *Chrysanthemum* plant:

1. Large daisy-type inflorescences with dark red-colored ray florets.
2. Strong, thick and upright flowering stems.
3. Uniform flowering habit.
4. Good postproduction longevity; plants maintain good substance for about 20 days in an interior environment.

Plants of the new *Chrysanthemum* differ from plants of the parent, 'Dektoshka' primarily in ray floret color as plants of 'Dektoshka' have red purple-colored ray florets.

Plants of the new *Chrysanthemum* can be compared to plants of *Chrysanthemum×morifolium* 'Timman Yellow', not patented. In side-by-side comparisons conducted in Hensbroek, The Netherlands, plants of the new *Chrysanthemum* differed from plants of 'Timman Yellow' in the following characteristics:

1. Plants of the new *Chrysanthemum* were less vigorous than plants of 'Timman Yellow'.
2. Plants of the new *Chrysanthemum* flowered about two days later than plants of 'Timman Yellow'.
3. Plants of the new *Chrysanthemum* had larger inflorescences than plants of 'Timman Yellow'.
4. Plants of the new *Chrysanthemum* and 'Timman Yellow' differed in ray floret color.

BRIEF DESCRIPTION OF THE PHOTOGRAPHS

The accompanying colored photographs illustrate the overall appearance of the new *Chrysanthemum* plant. These photographs show the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Dektoshka Red' grown as a spray-type.

The photograph on the second sheet comprises close-up views of the upper (top of photograph) and lower surfaces (bottom of photograph) of typical inflorescences and leaves of 'Dektoshka Red'.

DETAILED BOTANICAL DESCRIPTION

The aforementioned photographs and following observations and measurements describe plants grown during the winter in Hensbroek, The Netherlands, under commercial practice in ground beds in a glass-covered greenhouse. Plants were initially given 1.5 weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were nine weeks old when the photographs and the description were taken. In the following description, color references are made to The Royal Horticultural Society Colour Chart, 2007 Edition, except where general terms of ordinary dictionary significance are used.

Botanical classification: *Chrysanthemum×morifolium* 'Dektoshka Red'.

Parentage: Naturally-occurring whole plant mutation of *Chrysanthemum×morifolium* 'Dektoshka', not patented.

Propagation:

*Type.*—Terminal vegetative cuttings.

*Time to initiate roots, summer.*—About six days at 20° C.

*Time to initiate roots, winter.*—About seven days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous daisy-type cut flower that is typically grown as a spray-type; moderately vigorous growth habit.

*Flowering stem description.*—Aspect: Erect. Strength: Strong. Length: About 75 cm. Stem diameter: About 7 mm. Spray diameter: About 20 cm to 25 cm. Internode length: About 2.5 cm to 3 cm. Texture: Finely pubescent; longitudinally ridged. Color: Close to 146A.

*Foliage description.*—Arrangement: Alternate; simple. Length: About 8 cm to 11 cm. Width: About 4.5 cm to 6 cm. Apex: Broadly acute. Base: Attenuate. Margin: Palmately lobed, slightly serrate; sinuses parallel to divergent. Texture, upper and lower surfaces: Pubescent, slightly rough; veins prominent on lower surface. Venation pattern: Pinnate, reticulate. Color: Developing leaves, upper surface: Close to 137C. developing leaves, lower surface: Lighter than 147B. Fully developed leaves, upper surface: Close to 147A; venation, close to 148B. Fully developed leaves, lower surface: Close to 147B; venation, close to 147B to 147C. Petiole: Length: About 1 cm to 2.5 cm. Diameter: About 3 mm. Texture, upper and lower surfaces: Slightly rough. Color, upper surface: Close to 147B. Color, lower surface: Close to 146B.

Inflorescence description:

*Appearance.*—Daisy-type inflorescence form with obovate to oval-shaped ray florets and tubular disc florets; inflorescences borne perpendicular to axillary laterals (peduncles); ray and disc florets develop acropetally on a capitulum.

*Fragrance.*—Slightly fragrant.

*Flowering response.*—Under natural conditions, plant flower in the autumn/winter in the Northern Hemisphere; at other times of the year, inflorescence initiation and development can be induced under short day/long night conditions (at least 13.5 hours of darkness); uniform flowering response; plants exposed to 1.5 weeks of long day/short night conditions after planting followed by photoinductive short day/long night conditions flower about 52 days later when grown as a spray-type.

*Postproduction longevity.*—In an interior environment, inflorescences and foliage will maintain good color and substance for about 20 days; inflorescences persistent.

*Quantity of inflorescences.*—Grown as a spray type, about 20 inflorescences develop.

*Inflorescence size.*—Diameter: About 7 cm to 8 cm. Depth (height): About 2.5 cm. Disc diameter: About 1.5 cm. Receptacle height: About 5 mm. Receptacle diameter: About 6 mm. Receptacle color: Close to 145A to 145B.

*Inflorescence buds.*—Shape: Flattened spherical. Height: About 5 mm. Diameter: About 1 cm. Color: Close to 137C.

*Ray florets.*—Length: About 2.5 cm to 3.5 cm. Width: About 9 mm to 13 mm. Shape: Obovate to oval. Apex: Acute. Base: Attenuate. Margin: Entire. Texture, upper and lower surfaces: Smooth, glabrous; satiny. Number per inflorescence: About 30 to 35 arranged in about two to three whorls. Aspect: About 30° from horizontal. Color: When opening, upper surface: Close to 60A. When opening, lower surface: Close to 160D. Fully opened, upper surface: Close to 53A and towards the base, close to 6B; with development color becomes closer to 185B and towards the base, close to 8B. Fully opened, lower surface: Close to 160D with red purple-colored overlay; with development color becomes closer to 8D with red purple-colored overlay.

*Disc florets.*—Shape: Fused tubular, erect and elongated. Apex: Dentate. Length: About 3 mm to 5 mm. Diameter: About 1 mm. Number per inflorescence: About 350, massed at the center of the receptacle. Color: When opening: Apex: Close to 145A to 145B. Mid-section: Close to 12B. Base: Close to 145D. Fully opened: Apex: Close to 4A. Mid-section and base: Close to 145D.

*Involucral bracts.*—Length: About 6 mm to 10 mm. Width: About 2 mm to 6 mm. Shape: Ovate. Apex: Rounded. Base: Rounded to truncate. Margin: Entire. Texture, upper and lower surfaces: Smooth, glabrous. Number per inflorescence: About 35 arranged in about four whorls. Color, upper surface: Close to N137B. Color, lower surface: Close to N137A.

*Peduncles.*—Length, terminal peduncle: Terminal inflorescence bud removed to enhance spray development. Length, fourth peduncle: About 10 cm. Length, seventh peduncle: About 14 cm. Diameter: About 3 mm. Strength: Strong. Angle: About 30° from the flowering stem axis. Texture: Pubescent. Color: Close to 137A.

*Reproductive organs.*—Androecium: Not observed. Gynoecium: Present on both ray and disc florets. Style length: About 4 mm. Style color: Greenish. Stigma color: Yellow.

*Seed/fruit.*—Seed and fruit production have not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dektoshka Red' as illustrated and described.

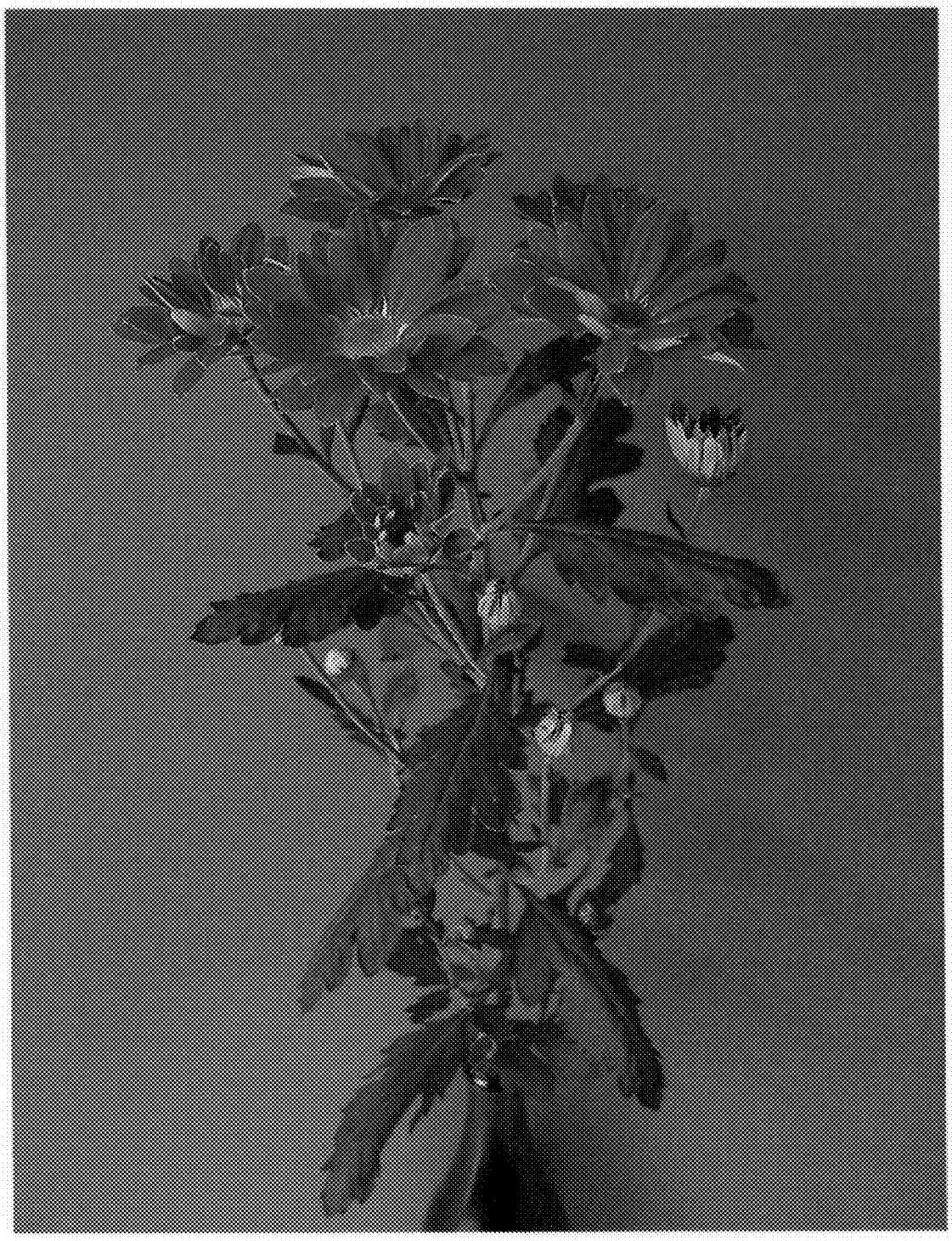

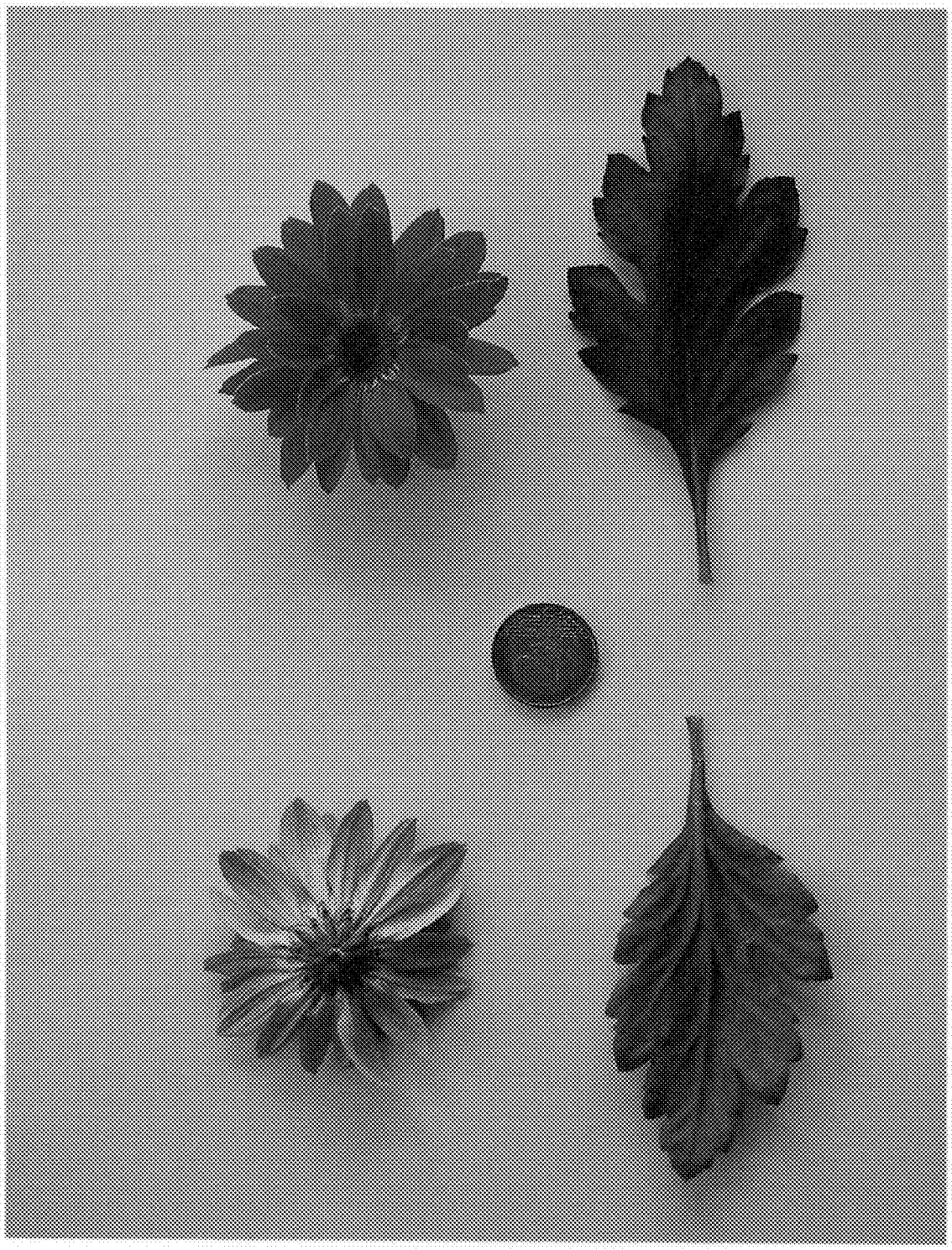

* * * * *